United States Patent [19]

Breidegam

[11] Patent Number: 4,813,459
[45] Date of Patent: * Mar. 21, 1989

[54] STRETCHABLE MATERIAL HAVING REDUNDANT CONDUCTIVE SECTIONS

[75] Inventor: Albert C. Breidegam, Sharpsburg, Ga.

[73] Assignee: Semtronics Corporation, Peachtree City, Ga.

[*] Notice: The portion of the term of this patent subsequent to Mar. 18, 2003 has been disclaimed.

[21] Appl. No.: 110,552

[22] Filed: Oct. 19, 1987

Related U.S. Application Data

[60] Continuation of Ser. No. 933,169, Nov. 21, 1986, abandoned, which is a division of Ser. No. 804,052, Dec. 2, 1986, Pat. No. 4,639,825, which is a continuation-in-part of Ser. No. 654,636, Sep. 25, 1984, Pat. No. 4,577,256.

[51] Int. Cl.4 .............................. D03D 15/08
[52] U.S. Cl. .................. 139/421; 139/420 C; 139/425 R; 361/220
[58] Field of Search ............... 139/421, 422, 425 R, 139/423; 361/220, 222, 223, 224

[56] References Cited

U.S. PATENT DOCUMENTS

| | | | |
|---|---|---|---|
| 1,531,862 | 3/1925 | Larned . | |
| 3,063,447 | 11/1962 | Kirsten | 128/134 |
| 3,172,430 | 3/1965 | Weidhaas | 139/422 |
| 3,377,509 | 4/1968 | Legge | 317/2 |
| 3,422,460 | 1/1969 | Burke et al. | 2/73 |
| 3,424,698 | 1/1969 | Lupinski et al. | 252/500 |
| 3,459,997 | 8/1969 | Legge | 317/2 |
| 3,541,389 | 11/1970 | Van Name | 317/2 |
| 3,582,448 | 6/1971 | Okuhasi | 161/87 |
| 3,596,134 | 7/1971 | Burke | 317/2 B |
| 3,699,590 | 10/1972 | Webber et al. | 2/73 |
| 3,812,861 | 5/1974 | Peters | 128/418 |
| 3,832,841 | 9/1974 | Cole | 57/152 |
| 3,851,456 | 12/1974 | Hamada et al. | 57/140 |
| 3,857,397 | 12/1974 | Brosseau | 128/384 |
| 3,858,622 | 1/1975 | Campbell et al. | 139/421 |
| 3,904,929 | 9/1975 | Kanaya et al. | 317/2 |
| 3,949,129 | 4/1976 | Hubbard | 428/190 |
| 3,986,530 | 10/1976 | Maekawa | 139/425 |
| 3,987,613 | 10/1976 | Woods et al. | 57/140 |
| 4,267,233 | 5/1981 | Tanaka et al. | 428/389 |
| 4,321,789 | 3/1982 | Dammann et al. | 57/224 |
| 4,373,175 | 2/1983 | Mykkanen | 361/220 |
| 4,398,277 | 8/1983 | Christiansen et al. | 361/220 |
| 4,402,560 | 9/1983 | Swainbank | 339/11 |
| 4,420,529 | 12/1983 | Westhead | 428/244 |
| 4,422,483 | 12/1983 | Zins | 139/420 |
| 4,459,633 | 7/1984 | Vandermark | 361/220 |
| 4,475,141 | 10/1984 | Antonevich | 361/220 |
| 4,605,984 | 8/1986 | Fiedler | 361/220 |
| 4,639,545 | 1/1987 | Pithouse et al. | 139/425 R |
| 4,654,748 | 3/1987 | Rees | 139/422 |
| 4,664,158 | 5/1987 | Sands | 139/422 |

FOREIGN PATENT DOCUMENTS

| | | |
|---|---|---|
| 2547390 | 5/1977 | Fed. Rep. of Germany . |
| 1067260 | 8/1965 | United Kingdom . |

Primary Examiner—Henry S. Jaudon
Attorney, Agent, or Firm—Kilpatrick & Cody

[57] ABSTRACT

A stretchable grounding strap for additional reliability in grounding the wearer's body through the use of two or more separate sections of conductive material, each of which is connected to ground by a separate grounding line. Circuitry utilized in connection with the strap senses loss of electrical contact between the strap and ground and provides visual and aural notification that contact is lost, as well as visual notification when the strap is grounded. According to one group of embodiments, the strap utilizes a stretchable material having two or more sections of longitudinally oriented electrically conductive fibers on its inner surface. Face yarns on its outer surface may form letters, words, logos or other pleasing or commercially attractive designs. Elastic yarns allow the material to stretch easily and comfortably. According to another group of embodiments, the strap comprises at least two sections of metal links. One or more clasps, which may be adjustable, are attached to the material, and fittings are mounted on the clasps, one fitting corresponding to each section of conductive material and for receiving one grounding cord.

4 Claims, 7 Drawing Sheets

STRETCHABLE MATERIAL HAVING REDUNDANT CONDUCTIVE SECTIONS

This is a continuation of my Ser. No. 06/933,169 filed Nov. 21, 1985 entitled STRETCHABLE MATERIAL HAVING REDUNDANT CONDUCTIVE SECTIONS which is in turn a division of my Ser. No. 06/804,062 filed Dec. 2, 1985 entitled STRETCHABLE GROUNDING STRAP HAVING REDUNDANT CONDUCTIVE SECTIONS, which issued as U.S. Pat. No. 4,639,825 on Jan. 27, 1987, which is in turn a continuation-in-part of my earlier Ser. No. 06/654,636 Filed Sept. 25, 1984 entitled WOVEN STRETCHABLE GROUNDING STRAP, which issued as U.S. Pat. No. 4,577,256 on Mar. 18, 1986.

BACKGROUND OF THE INVENTION

This invention pertains to a strap that may be comfortably worn on the arm or leg and that has two or more sections of conductive material for improved wicking of static electrical charges from the wearer's body.

Static electricity begets problems in the electronics and other industries, particularly with the advent of integrated circuits and other microelectronic components. Components such as integrated circuits, for instance, may be disabled or destroyed by over-voltages or power density resulting from static electricity. Certain junctions in such circuits can be destroyed by as little as a 50 volt potential, which radically changes the doping structure in their lattices. Power densities resulting from excessive potential and imperfections in circuit layout or structure can vaporize or radically alter the silicon substrate and thus impair or destroy a circuit's performance. Yet a person walking on carpet on a dry day can accumulate as much as 30,000 volts of potential, and he can triboelectrically generate thousands of volts by simply changing his position in his chair or handling a styrofoam cup.

Such a person can inadvertently discharge such static potential into a circuit or component by touching it and causing over-voltage or excessive power density. Additionally, the potential in such a person's body can induce a charge in a circuit that can later cause overvoltage or excessive power density when the circuit is subsequently grounded.

More and more frequently, therefore, those in industries in which integrated circuits and other microelectronic components are handled or assembled are taking measures to limit the failure rate of those circuits and components by attempting to keep them as well as their environment at zero electrical potential. Such measures include providing workers and work stations with antistatic carpet, conductive or dissipative grounded desk top work surfaces, hot air ion generators which emit ions to neutralize static charges, and grounding straps to keep workers at zero potential.

The term "conductive" herein, and according to its customary usage in the art, means an electrical resistance of between zero and $10^5$ ohms. Similarly, "dissipative" means a resistance of between $10^5$ and $10^9$ ohms, "antistatio" means a resistance of between $10^9$ and $10^{14}$ ohms, and "insulative" means a resistance of more than 10 ohms.

The situations in which grounding straps are used heighten the importance of their being reliable in maintaining continuous electrical contact with the skin. The person working on microelectric components or integrated circuits may be completely unaware that he has accumulated minor static electrical charges, and may therefore unknowingly be in a position to disable circuits on which he is working or which he is handling. If his strap is loose or he has removed it, he may be unaware that electrical discharges transmitted from his fingers are disabling the circuits. (A typical person cannot sense a static electrical discharge of less than approximately 3,500 volts.) No one may discover that the circuits have been disabled or damaged until hours, days, or weeks later, when the circuits have been placed in components or devices which fail in the field. Removal and repair or replacement of these circuits once in the field is far costlier than avoiding potential failure while the wearer is handling the circuits. Thus, the wearer's employer typically must depend upon the effectiveness of the wrist strap to maintain a lower failure rate of such electronic circuits and components by maintaining continuous electrical contact with the wearer's wrist and by providing the wearer with minimum temptation to remove the strap from his wrist.

Comfort is important, not only for its own sake, but also because it increases the reliability of the strap in grounding the user's body. If the strap is uncomfortable, the wearer will be tempted to remove it and can thereby cause damage to electrical circuits and components on which he is working. A strap that is easily stretchable, that breathes, that is attractive and that poses minimum inconvenience to the wearer is therefore highly desired.

In the past, stretchable grounding straps have typically utilized a single conductive surface on the inside of the strap which contacts the skin. That conductive surface is electrically connected to a grounding cord which leads from the strap to a grounded electrical connection.

These considerations have been addressed by several types of grounding straps. U.S. Pat. No. 4,373,175 issued Feb. 8, 1983 to Mykkanen, for instance, discloses an extensible metal band similar to a "Speidel" watchband on which a snap fastener for a grounding cord is attached. Such a strap includes only one contact and line connecting the strap with ground, however, and its conductive metal outer surface can prove dangerous to the wearer if it contacts an electrical potential sufficient to electrocute the wearer. Further, the Mykkanen strap includes no visual or aural means to inform the wearer when the strap loses electrical connection with ground.

Another grounding strap is disclosed in U.S. Pat. No. 3,857,397 issued Dec. 31, 1974 to Brosseau. Outer and inner conductive polyolefin layers sandwich an intermediate nylon scrim layer to form the band. Hook and loop ("Velcro") fastening material holds the strap on the wrist. This strap is typical of a number of straps having carbon-suffused synthetics or other conductive polyolefins. Body oils and minerals can accumulate on such surfaces and interfere with electrical contact between the band and the skin. Further, the Brosseau strap includes only one electrical contact surface and grounding line, and that patent discloses no visual or aural means to inform the wearer the strap has lost electrical connection with ground.

Another approach to many of these problems is disclosed in U.S. Pat. No. 4,398,277 issued Aug. 9, 1983 to Christiansen and Westberg. This strap is made of knitted stretchable fabric containing stainless steel fibers. A plastic and metal fitting permanently closes the strap into a loop of predetermined size and has a connection for a grounding cord. As in the case of the straps mentioned above, the Christiansen strap includes only one electrical contact surface and grounding line, and no visual or aural means is disclosed for informing the wearer that the strap has lost electrical connection with ground.

SUMMARY OF THE INVENTION

The stretchable grounding strap of the present invention achieves additional reliability in grounding the wearer's body through the use of two or more separate sections of conductive material, each of which is connected to ground by a separate grounding line. Circuitry utilized in connection with the strap senses loss of electrical contact between the strap and ground and provides visual and aural notification that contact is lost. Such circuitry may also continuously notify the wearer when his body is electrically connected with ground.

The strap utilizes a stretchable material having two or more electrically conductive sections on its inner surface. In one group of embodiments, the conductive sections are of metallic or conductive fibers and face yarns on the outer surface may form letters, words, logos or other pleasing or commercially attractive designs. Elastic yarns allow the material to stretch easily and comfortably. One or more clasps are attached to the material, and fittings are mounted on the clasps, one fitting corresponding to each section of conductive material. for receiving the grounding lines. In a second group of embodiments, a plurality of metallic links separated into sections by nonconductive materials form the expandable strap and are non-conductive on their outer surface.

It is therefore an object of this invention to provide an inexpensive stretchable grounding strap that has two sections of electrically conductive material each of which may independently be connected to ground for additional reliability.

It is an additional object of this invention to provide an inexpensive stretchable grounding strap with related circuitry which gives a visual and aural warning when the electrically conductive sections lose contact with ground, and a visual notification when the sections are in contact with ground.

It is an additional object of this invention to provide an inexpensive stretchable grounding strap that is comfortable and adjustable in size, so that wearers will be less tempted to remove it or impair its effectiveness than during use of previous straps.

It is another object of this invention to provide a stretchable grounding strap on the outer surface of which may be placed letters. words, logos, or other attractive designs.

It is a further object of this invention to provide a stretchable grounding strap that is not electrically conductive on its outer surface.

It is a further object of this invention to provide a woven stretchable grounding strap that does not become narrower when stretched, that stretches more easily than knitted fabrics and that does not roll over onto itself as it is being drawn over the hand.

It is a further object of this invention to provide a stretchable grounding strap comprising two sections of metal links which avoids problems associated with stray metallic fibers and thus which is particularly appropriate for use in "clean room" environments.

Other objects, features and advantages of this invention will be apparent in the specifications, claim drawings herein.

DETAILED DESCRIPTION OF THE DRAWINGS

Figure 1:
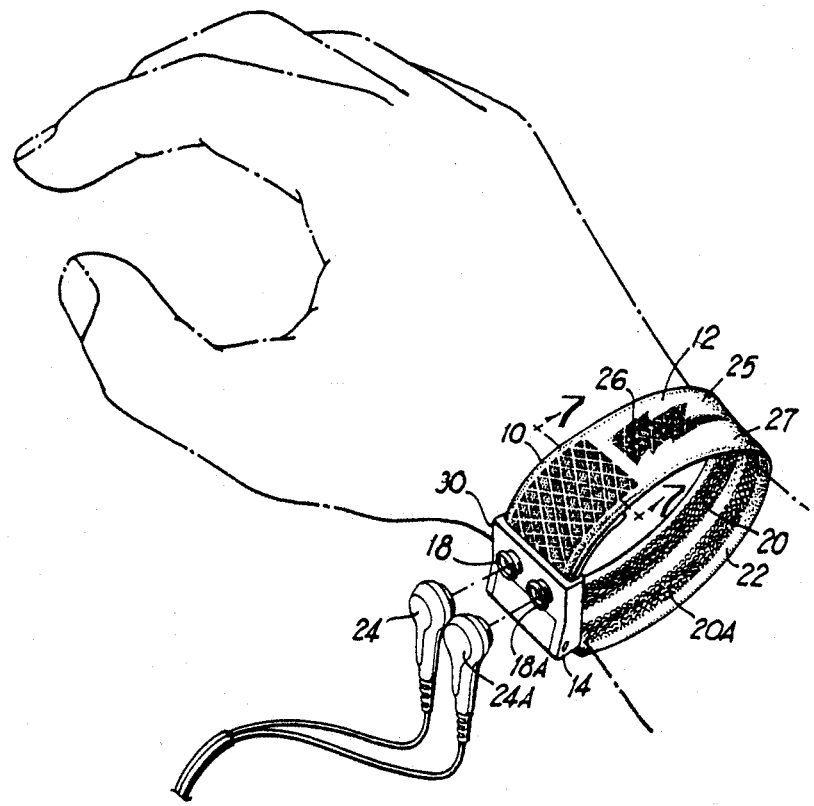
FIG. 1 is a perspective view of a preferred embodiment of a stretchable grounding strap of this invention.

FIG. 1 illustrates one preferred embodiment of the strap of this invention. Material 12 of strap 10 is connected to a clasp 14. Two fasteners 18 and 18A are mounted on clasp 14 and electrically connected, respectively, to sections of conductive yarns 20 and 20A on the inner surface 22 of material 12. Each fastener 18 and 18A receives a grounding cord or line 24 and 24A. Grounding cords 24 and 24A, which may contain a one megaohm resistor to prevent electrical shock if grounding cord 24 or 24A contacts a power source, carries body electrostatic charges from the wearer's wrist to electrical ground. Face yarns 25 on the outer surface 27 of material 12 may impart a design 26 on outer surface 27. Design 26 improves the appearance and marketability of strap 10. Face yarns 25 may be of various colors and may form designs 26 including letters, words, logos or other aesthetically pleasing or commercially desirable configurations. Clasp 14 may be configured in a conventional manner to make strap 10 adjustable; alternatively, it may be adjustably configured as is disclosed in FIGS. 2-4 and the accompanying text of my application for U.S. Patent entitled "WOVEN STRETCHABLE GROUNDING STRAP" filed Sept. 25, 1984 and having Ser. No. 06/654,636. which application is incorporated herein by this reference.

Figure 2:
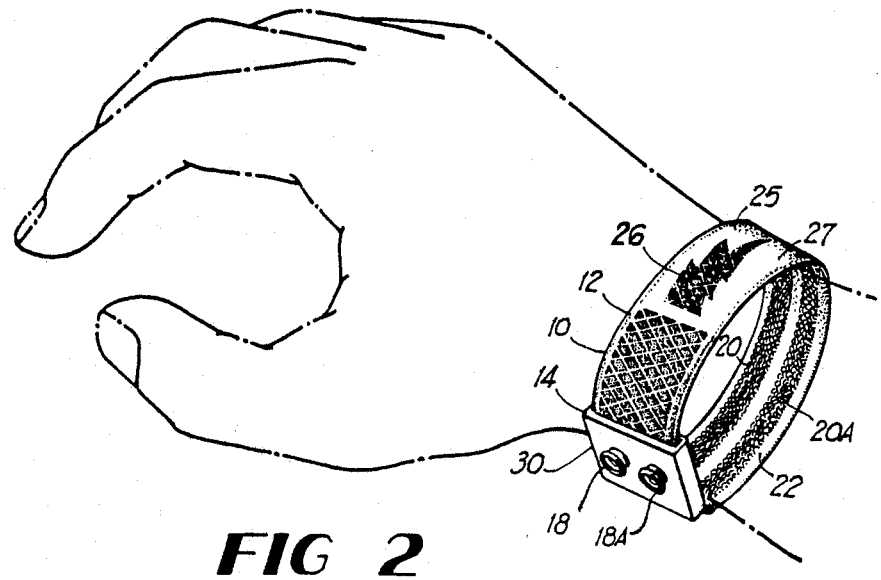
FIG. 2 is a perspective view of a second embodiment of a stretchable grounding strap of this invention.
Figure 3:
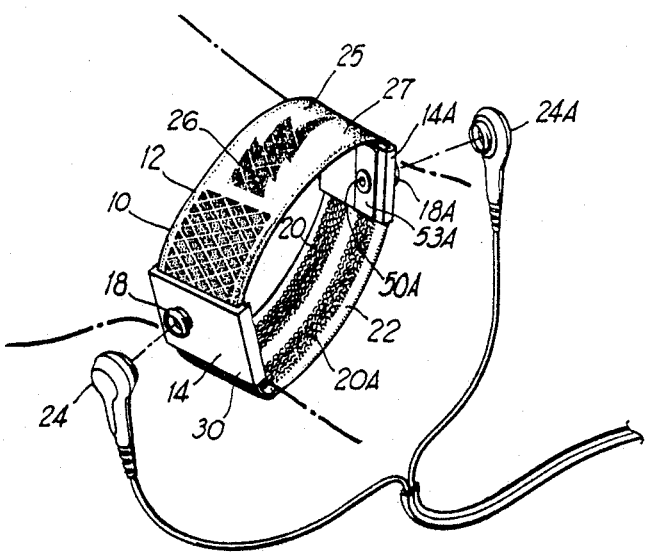
FIG. 3 is a perspective view of a third embodiment of a stretchable grounding strap of this invention.
Figure 4:
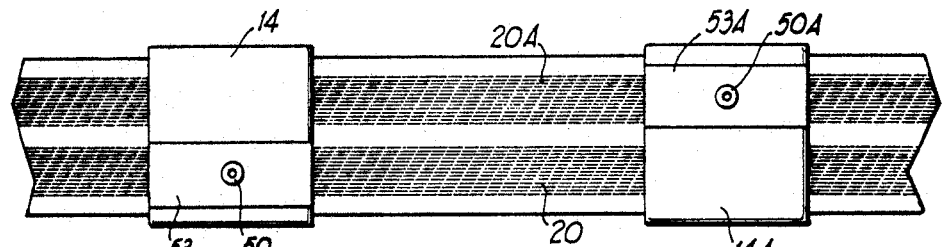
FIG. 4 is a plan view of a portion of the side of the strap of FIG. 3.
Figure 13:
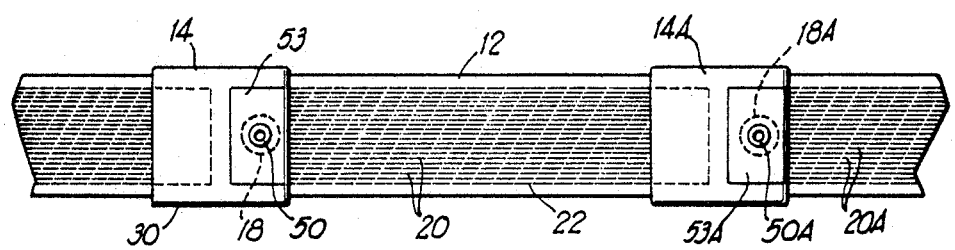
FIG. 13 is a plan view of a portion of the strap of FIG. 12.
Figure 14:
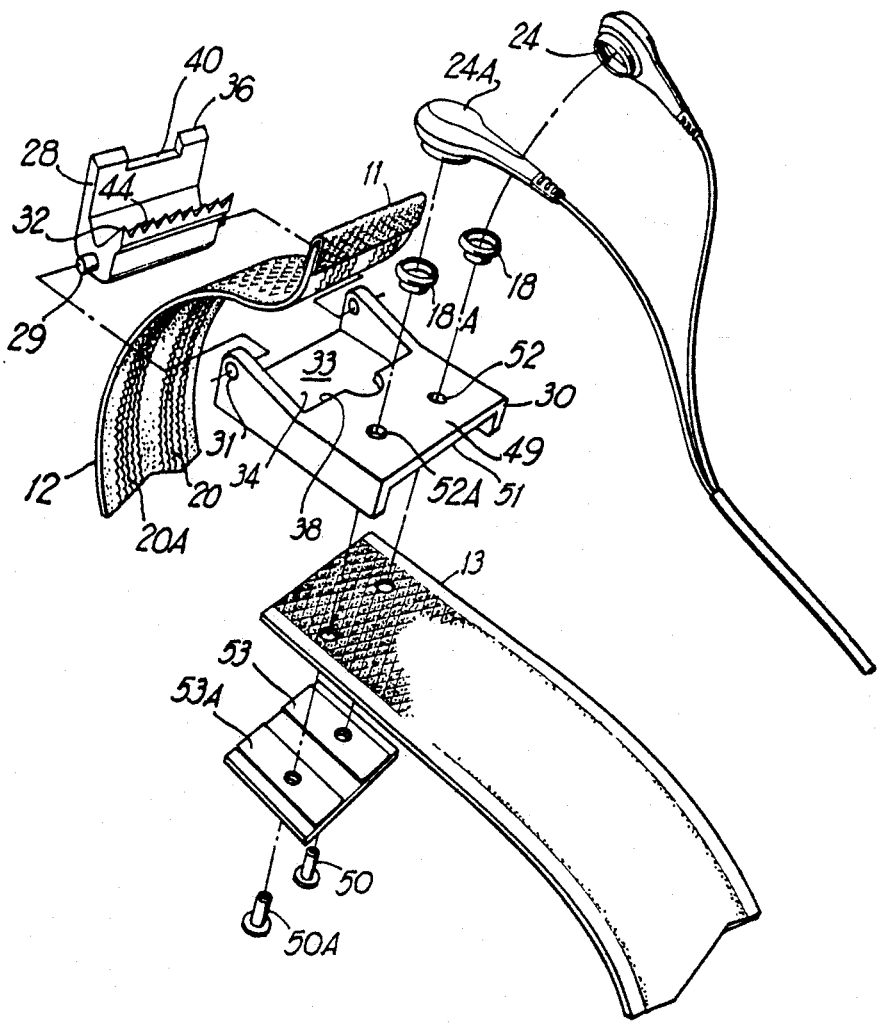
FIG. 14 is a perspective view of an adjustable clasp according to this invention.

In this regard, FIG. 14 shows more clearly the clasp 14 of the strap 10 of FIG. 1 which corresponds generally to the clasps illustrated in FIGS. 2-4 of my earlier above-referenced application. A gate 28 is pivotally mounted in a clasp body 30 by pins 29 and pin holes 31 to capture material 12 when desired. Jam 32 on gate 28 forces second end 11 of material 12 against the bottom 33 of recess 34 of body 30 when gate 28 is closed in position. Edge 36 of gate 28 is biased against and cooperates with lip 38 of body 30 to hold gate 28 shut. Edge 36 may have a recess 40 to make it easier to snap gate 28 shut, and jam 32 may have teeth 44 to allow it to grip more tightly second end 11 of material 12. Clasps 14 and 14A may also be adjustable as disclosed in FIGS. 7-13 of my earlier application for United States Patent entitled "WOVEN STRETCHABLE GROUNDING STRAP" filed Sept. 25, 1984 and having Ser. No. 06/654,636.

In a second embodiment shown in FIG. 2, clasp 14 is non-adjustable, in which event strap 10 may be manufactured in varying sizes to fit various wrist sizes. FIG. 3 illustrates a third embodiment of strap 10 in which two clasps 14 are used, and are positioned approximately diametrically opposite one another. In this embodiment, one fastener 18 connected to a section of conductive yarns 20 is located on the first clasp 14, while the second fastener 18A connected to a section of conductive yarns 20A is located on clasp 14A. This configuration provides added protection against a clasp malfunction which might cause failure of the single clasp configurations of FIGS. 1 and 2.

In all configurations of clasps 14 and 14A, plates 53 and 53A of metallic material may be located on the interior surface of clasp 14 or clasps 14 and 14A, to add additional strength and anchoring for fasteners 18 or 18A, and to provide an additional source of electrical contact between strap 10 and the wearer's body.

Whatever the structure of clasp 14 or 14A, clasp body 30 should be made of anti-static material to minimize risk of inadvertent electrical contact of a conductive clasp with an electrical power source and subsequent electrocution of the wearer, while simultaneously avoiding unwarranted generation of static electricity on the clasp that could occur if the clasp were made of insulated material. Yet clasp 14 or 14A should be made of material hard enough to capture material 12 firmly and resilient enough to be sufficiently durable. In the preferred embodiment, clasp body 30 is of nylon. which because of its hygroscopic properties is anti-static, but other suitable polymeric materials may be used.

Clasp 14 and 14A also serve as a mounting base for one or more grounding cords 24 and 24A connected to fasteners 18 and 18A. In the preferred embodiment, fasteners 18 and 18A are free swivel snaps physically connected to the outer, first surface 49 of clasp body 30 by rivet 50 and 50A passing through opening 52 and 52A in clasp body 30. Metallic plates 53 and 53A and first end 13 of woven material 12 are also connected to the interior surface of body 30 by rivets 5D and 50A, which pass through holes in each of them. Metallic plates 53 and 53A may be of any suitable corrosion resistant metal, and serve as an additional electrical contact with the wearer's wrist, as well as holding material 12 against the inner, second surface 51 of clasp body 30. In the preferred embodiment, plates 53 and 53A are of stainless steel.

Figure 5:
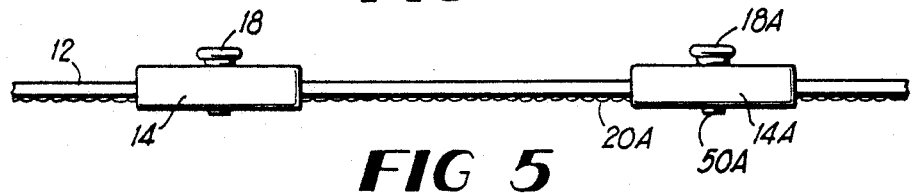
FIG. 5 is a side elevational view of the portion of the strap of FIG. 4.
Figure 6:
FIG. 6 is a bottom plan view of the portion of the strap of FIG. 4.

FIGS. 4-6 are top plan, side elevational and bottom plan views of the material 12 of strap 10 shown in FIG. 3. As those figures clearly illustrate, each section of conductive yarns 20 or 20A corresponds to its own fastener 18 or 18A and, where used, metallic plate 53 or 53A.

The sections of conductive yarns 20 and 20A in the embodiments shown in FIGS. 1-3 are essentially parallel to one another and run longitudinally through the strap. They may extend around the entire circumference of strap 10, or for only a portion of the circumference. Accordingly, material 12 may be manufactured having two or more parallel conductive sections 20 and 20A and additional sections, or the apparatus utilized to manufacture material 12 may be configured intermittently or serially to weave. knit or otherwise form into material 12 such conductive sections which will not extend the entire length of material 12 or around the entire circumference of the strap 10.

Figure 12:
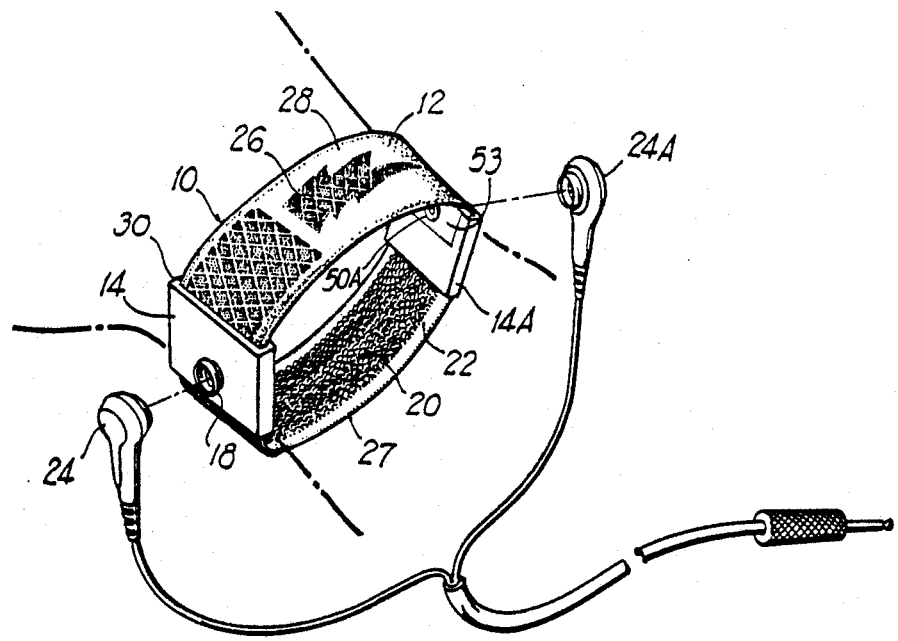
FIG. 12 is a perspective view of a fourth embodiment of a stretchable grounding strap of this invention.

Alternatively, conductive sections 20 and 20A may be formed on the inner surface 22, not parallel to one another as shown in FIGS. 1-3. but located on different sides of the strap from one another as shown in FIGS. 12 and 13. In this second group of embodiments, sections 20 and 20A may be formed in material 12 in serial fashion and to have greater width than the sections 20 and 20A which are formed in material 12 in parallel fashion as shown in FIGS. 1-3. Such sections 20 and 20A may be formed in material 12 by intermittently or serially weaving, knitting or otherwise forming conductive yarns in material 12, or simply by utilizing two or more independent lengths of material 12 to form the circumference of strap 10, each length having its independent section 20 or 20A of conductive yarns.

Sections 20, 20A and additional sections may also be formed in parallel fashion as shown in FIGS. 1-3 in material 12, and extend for only a portion of the circumference of the strap as shown in FIGS. 12 and 13, thus falling within a hybrid of the two general categorizations of conductive yarn section 20 configurations illustrated by FIGS. 1-3 and FIGS. 12 and 13, respectively. In any of these configurations, two or more sections 20, 20A and additional sections may be utilized. More than two suc sections will likely best be accommodated by a single clasp as in FIGS. 1 or 2, but two or more clasps may be used.

Material 12 may be knitted or woven fabric or other suitable elastic material. Knitted material 12 may be of the type disclosed in U.S. Pat. No. 4,398,277 issued Aug. 9, 1983 to Christensen and Westberg, which patent is incorporated herein by this reference. Preferably, however, material 12 is woven fabric, to reduce variations in conductivity of conductive yarns sections 20 and 20A during stretching of the strap, because woven straps do not become thinner while stretched as do typical knitted straps, and for other reasons.

Figure 7:
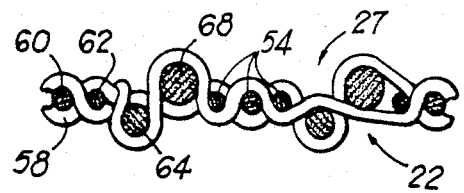
FIG. 7 is an enlarged partial cross-sectional view of a portion of a longitudinal cross-section of the material of the strap of FIG. 1 taken along lines 7—7 of the strap of FIG. 1.
Figure 8:
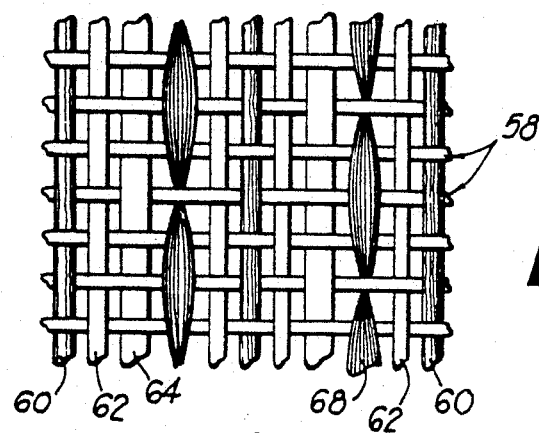
FIG. 8 is an enlarged plan view of a portion of an electrically conductive section of the strap of FIG. 1.

FIGS. 7 and 8 show more fully the structure of woven material 12. FIG. 7 is a cross-sectional view taken along line 7—7 of FIG. 1, looking longitudinally into a section of conductive yarns 20 or 20A of material 12. The yarns shown in cross-section are warp yarns 54, while those shown extending around warp yarns 54 are weft yarns 58. Weft yarns 58 may be made of filament nylon or other synthetic or naturally insulative material. In the preferred embodiment, weft yarns 58 are substantially nonstretchable, so that material 12 and strap 10 do not stretch in the lateral direction.

Warp yarns 54 comprise elastic yarns 60, binder yarns 62. conductive yarns 64 and face yarns 68. Elastic yarns 60 and binder yarns 62 interweave with the weft yarns 58 in a one-up, one-down pattern to form the body of material 12, while conductive yarns 64 are arranged in repetitive floats under the weft so as to appear on inner surface 22, and face yarns 68 are arranged in repetitive floates over thw weft so as to appear on outer surface 27 of strap 10. In the arrangement shown, conductive yarns 64 pass under three wefts and over one, while face yarns 68 pass over three wefts and under one. Yarns 60, 62, 64 and 68 are arranged sequentially across the width of the section. Material 12 is thus conductive on portions of its inner surface 22 and face yarns 68 form designs 26 on its outer surface 27. Material 12 may be woven in extended or partially extended state to allow conductive yarns 64 and face yarns 68 to extend continuously longitudinally through material 12 when stretched to form bights or loops when material 12 is relaxed.

Elastic yarns 60 may be formed of stretchable fibers such as spandex fibers or they may be formed of a rubber thread or threads. In the preferred embodiment, elastic yarns 60 are of rubbar triple wrapped with polyester. Alternatively, spandex fibers may be used, or spandex fibers may be combined with other natural or synthetic fibers to form elastic yarns 60.

Binder yarns 62 add body to material 12 and serve additionally to insulate electrically conductive yarns 64 from outer surface 27 of material 12. They may be formed of any suitable insulated material and in the preferred embodiment are of spun polyester.

Conductive yarns 64 contact the wearer's skin and conduct static electrical charges to metal plates 53 and 53A and rivets 50 and 50A, which are electrically connected to ground through fasteners 18 and 18A and cords 24 and 24A. Conductive yarns 64 may be formed of stainless steel fibers such as Bekitex, supplied by the Bekaert Company of Belgium and described in U.S. Pat. No. 3,987,613, which patent is incorporated herein by this reference.

Such fibers may be combined with other fibers to form conductive yarns 64, including polyester. nylon or other synthetic or natural fibers. Copper fibers or other metallic or carbon suffused fibers may be used rather than or in combination with stainless steel fibers.

Face yarns 68 serve as insulators and to decorate the outer surface 27 of strap 10. Face yarns 68 are preferably of spun polyester, but may be formed of nylon or other synthetic or natural fibers. Weaving of weft yarns 58 and face yarns 68 may be arranged to form designs 26 on outer surface 27, and face yarns 68 may comprise varying colors to impart either a monochrome or multicolor design 26. Material 12 may be woven on any conventional weaving equipment on which elastic tape is woven, thereby further reducing manufacture expense.

In use, when the clasp of FIG. 14 is used, the wearer pulls strap 10 over his or her hand and onto his or her wrist, and, where appropriate, draws material 12 through clasp 14 until strap 10 is comfortably snug about the wrist and then closes gate 28 loosely to grasp second end 11 of material 12. He or she then marks material 12 parallel to edge 36 of gate 28 and cuts second end 11 of material 12 off at this point. The remaining portion of material 12 is then placed in recess 34 and gate 28 is closed tightly so that edge 36 is biased against lip 38 to hold gate 28 in place. Jam 32 will then prevent material 12 from escaping clasp 14. These steps are unnecessary where clasps 14 and 14A are not adjustable. Analogous steps may be used for conventional adjustable clasps.

Figures 15, 16:
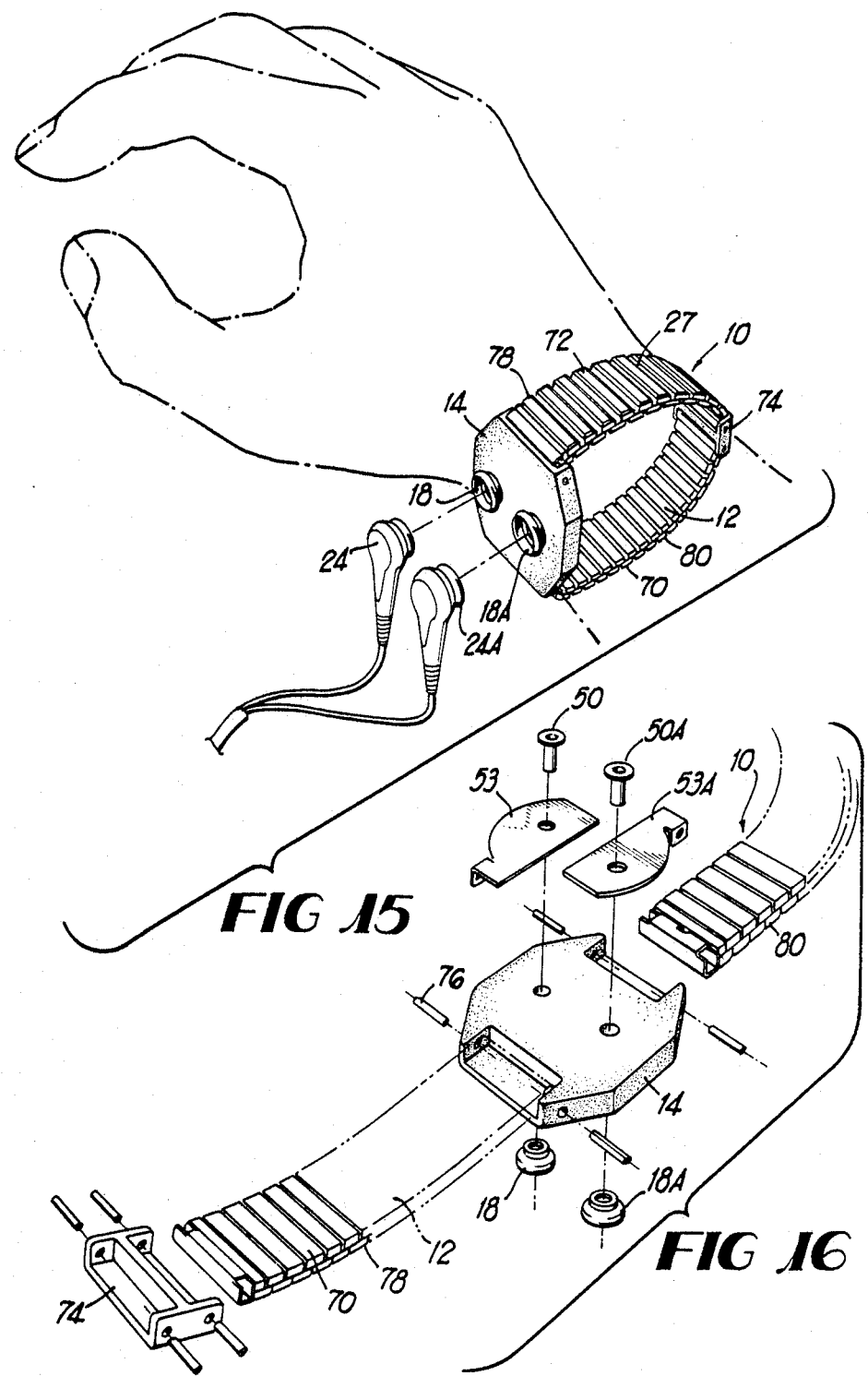
FIG. 15 is a perspective view of a fifth embodiment of a stretchable grounding strap of this invention comprising metallic links.
FIG. 16 is a perspective view of a portion of the interior side of the strap of FIG. 15.

FIGS. 15 and 16 illustrate an additional group of embodiments of straps 10 according to the present invention. According to this group of embodiments, a plurality of metallic links 70 forms the material 12 of strap 10. Metallic links 70 may be of stainless steel or other appropriate metal. and in one embodiment are provided in the form of strap material by Speidel Corporation. Metallic links 70 are covered on the sides facing outer surface 27 of strap 10 with non-conductive material 72. Straps 10 may be provided in various sizes to minimize separation of adjacent metallic links 70 when worn in order to minimize the possibility that an electrically charged instrument may penetrate between two adjacent links and contact a conductive portion of material 12.

Material 12 comprising metallic links 70 is attached to clasp 14 at one end and to a non-conductive link 74 at the other end to form a first section 78 of conductive material 12 to contact the wearer's body. Another section of material 12 is similarly connected to the other side of clasp 14 and non-conductive link 74 to form a second section 80 of conductive material 12.

As in the above-mentioned embodiments, clasp 14 and non-conductive link 74 may be formed of any non-conductive or anti-static material. but are preferably nylon because of its hygroscopic properties.

Sections 78 and 80 of material 12 comprising metallic links 70 are connected to clasp 14 by pins 76 similar to the conventional fashion in which watch bands are connected to watches.

Grounding cords 24 and 24A which connect the strap to ground are connected to first and second sections 78 and 80 through a set of fasteners 18 and 18A, rivets 50 and 50A and metallic plates 53 and 53A. As shown in FIG. 16, a first metallic plate 53 contacts first section 78 of material 12 and is held in place by rivet 50. Rivet 50 is connected to fastener 18 which may be a snap connector as disclosed above to receive grounding cord 24. Metallic plate 53A similarly contacts second section 80 and is held in place by rivet 50A connected to fastener 18A. As disclosed above, plates 53 and 53A are preferably of stainless steel because it is corrosion resistant and provides additional electrical contact with the wearer's skin.

After strap 10 has been placed about the wearer's wrist, grounding cords 24 and 24A are connected to fasteners 18 and 18A.

Figure 9:
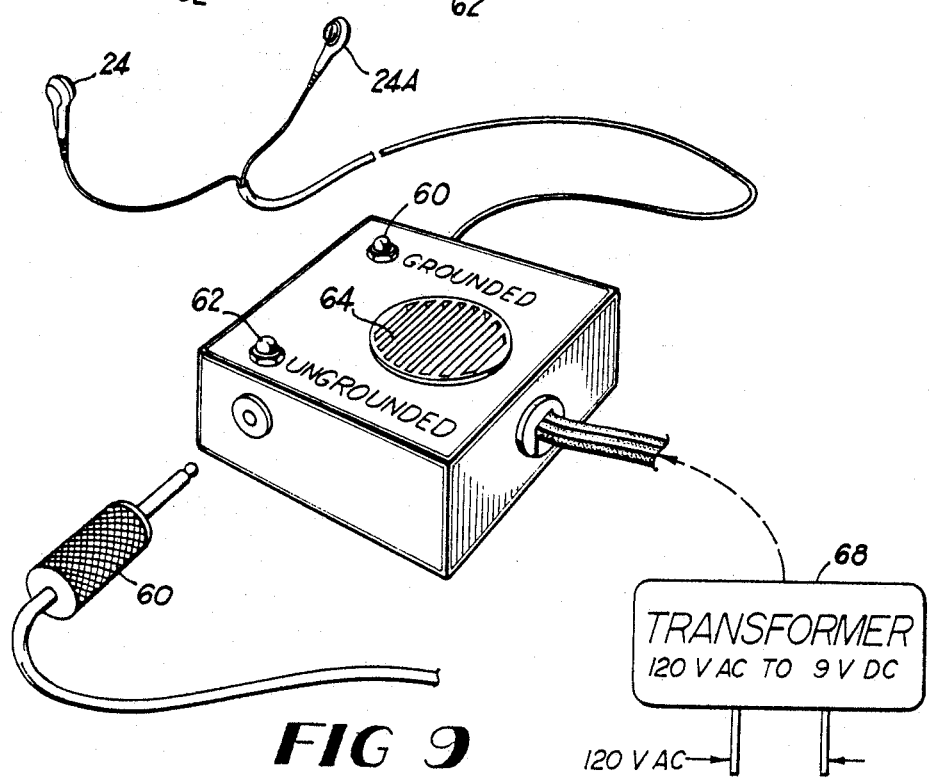
FIG. 9 is a perspective view of one embodiment of a component for housing the circuitry of the present invention which provides visual and aural warning when electrical contact between the strap and ground is lost and visual notification when the strap is grounded.

Grounding cords 24 and 24A may be directly connected to ground or they may be indirectly connected to ground by means of circuitry 56 which provides visual and aural warning when electrical contact is lost between strap and ground, and visual notification when strap 10 is in contact with ground. A housing 58 for such circuitry 56 is shown in FIG. 9. Green light emitting diode ("LED") 60, red LED 62 and piezoelectric screamer 64 are mounted on housing 58 to provide such warning. Green LED 60 provides positive notice that strap 10 is in electrical connection with ground. When such contact is lost, green LED 60 is extinguished. red LED 62 illuminates, and screamer 64 sounds. As shown in FIG. 9, grounding cords 24 and 24A may be connected to circuitry 56 and housing 58 by a co-axial jack 66. Circuitry 56 is powered by a power supply 68, which in the preferred embodiment is 9-volt direct current output.

Figure 10:
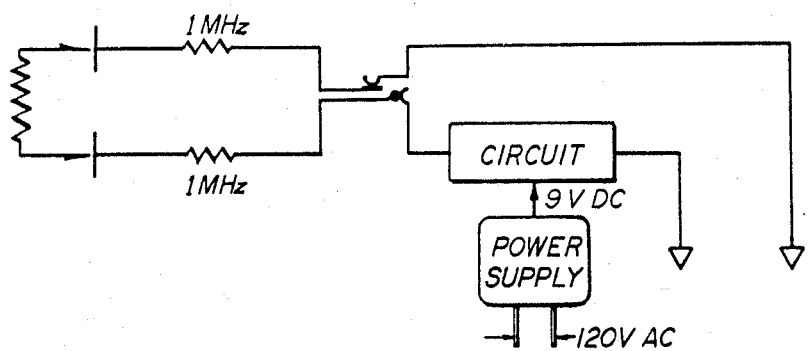
FIG. 10 is a schematic diagram showing the electrical connection between the strap of the present invention and ground.

FIG. 10 shows a schematic representation of strap 10, the one megaohm resisters in grounding cords 24 and 24A, and their connection with circuitry 15 and directly to ground.

Figure 11:
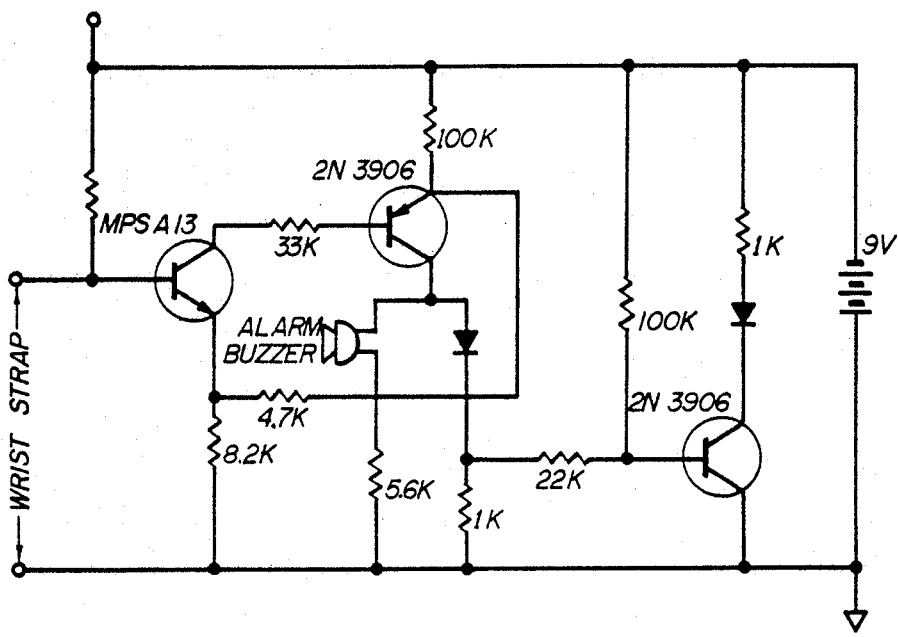
FIG. 11 is a schematic diagram showing one embodiment of circuitry of the present invention which provides visual and aural warning in the event the strap loses electrical contact with ground and visual notification when the strap is grounded.

FIG. 11 shows conventional sensing circuitry 56 which detects a significant increase in resistance caused by a break in electrical contact between strap 10 and ground and activates red LED 62 and screamer 64 while deactivating green LED 60. In the preferred embodiment, screamer 64 is a Murata Piezo Buzzer, and the resistors are ¼ watt film type with 5% tolerance.

After the wearer has placed the strap 10 around his or her wrist and connected grounding cords 24 and 24A to fasteners 18 and 18A, he or she plugs coaxial jack 66 into housing 58 and applies power to circuitry 56. Green LED 60 will activate if strap 10 is in electrical contact with ground, informing the wearer that strap 10 is performing its intended function of wicking away static electrical potential from his body.

The foregoing description of this invention is for purposes of explanation and illustration. It will be apparent to those skilled in the relevant art that modifications and changes may be made to the invention as thus described without departing from its scope and spirit.

I claim:

1. An elastic fabric having a plurality of non-conductive longitudinally extending sections and a plurality of conductive longitudinally extending sections, each said conductive section comprising:
   (a) a plurality of weft yarns extending transversely in the material and appearing on the inner and outer surface of the material;
   (b) a plurality of elastic warp yarns, each extending longitudinally in the material and engaged with the weft yarns in a one-up, one-down arrangement;
   (c) a plurality of binder warp yarns, each extending longitudinally in the material and engaged with the weft yarns in a one-up, one-down arrangement;
   (d) a plurality of face warp yarns, each extending longitudinally in the material and engaged with the weft yarns in a three-up, one-down arrangement, so as to appear on the outer surface of the material;
   (e) a plurality of sections of conductive warp yarns, each engaged with the weft yarns in a one-up, three down arrangement so as to appear on the inner surface of the material; the conductive yarns being separated by at least a binder warp yarn, an elastic warp yarn and a face warp yarn.

2. An elastic fabric according to claim 1 in which the conductive sections extend the length of the fabric and are parallel to one another.

3. An elastic fabric according to claim 1 in which the conductive warp yarns are formed of stainless steel fibers.

4. An elastic fabric according to claim 1 in which the electrically conductive yarns are formed of carbon suffused synthetic material.

* * * * *